(12) United States Patent
Ouchi

(10) Patent No.: US 6,878,108 B2
(45) Date of Patent: Apr. 12, 2005

(54) INSERTION UNIT FOR ENDOSCOPE

(75) Inventor: Teruo Ouchi, Saitama-ken (JP)

(73) Assignee: PENTAX Corporation, Tokyo (JP)

(*) Notice: Subject to any disclaimer, the term of this patent is extended or adjusted under 35 U.S.C. 154(b) by 385 days.

(21) Appl. No.: 10/042,157

(22) Filed: Jan. 11, 2002

(65) Prior Publication Data

US 2002/0137985 A1 Sep. 26, 2002

(30) Foreign Application Priority Data

Jan. 16, 2001 (JP) .......................................... 2001-007177

(51) Int. Cl.$^7$ ................................................. A61B 1/04
(52) U.S. Cl. ........................................ 600/130; 600/139
(58) Field of Search ................................ 600/101, 128, 600/129, 130, 139

(56) References Cited

U.S. PATENT DOCUMENTS 4,784,464 A 11/1988 Ouchi
6,585,639 B1 * 7/2003 Kotmel et al. .............. 600/116

FOREIGN PATENT DOCUMENTS

| JP | 54-18094 | 2/1979 |
|----|----------|--------|
| JP | 63-48243 | 12/1988 |
| JP | 3-42895 | 6/1991 |
| JP | 6-17945 | 3/1994 |
| JP | 7-85129 | 9/1995 |

* cited by examiner

*Primary Examiner*—Beverly M. Flanagan
(74) *Attorney, Agent, or Firm*—Greenblum & Bernstein, P.L.C.

(57) ABSTRACT

An insertion unit for an endoscope includes a flexible tube having an inner diameter $D_1$ and an inner cross-sectional area S, and a plurality of components inserted and arranged in said flexible tube. The plurality of components include at least one optical fiber bundle. The insertion unit is configured such that the inner diameter $D_1$ is not less than 6.5 mm and the inner cross-sectional area S satisfies the condition of $0.5 \leq \Sigma s/s \leq 0.6$, where $\Sigma s$ represents a sum of cross-sectional areas of the components arranged in the flexible tube. Alternatively, the insertion unit is configured such that the inner diameter $D_1$ is less than 6.5 mm and the inner cross-sectional area S satisfies the condition of $0.5 \leq \Sigma s/s \leq 0.65$.

6 Claims, 6 Drawing Sheets

INSERTION UNIT FOR ENDOSCOPE

BACKGROUND OF THE INVENTION

The present invention relates to an insertion unit for an endoscope accommodating a plurality of components such as tubes and bundles of optical fibers.

An endoscope has an insertion unit which is to be inserted into a human cavity. The insertion unit generally includes a flexible tube provided at a distal end portion thereof. Generally, the flexible tube is bendable by operation at an operation unit formed at a proximal end portion of the endoscope. Inside the flexible tube, a plurality of components such as tubes and bundles of optical fivers are accommodated.

The flexible tube is configured such that the diameter thereof is as small as possible so as not to provide much pain to a patient during an endoscopic inspection. On the other hand, the diameter of the flexible tube is also determined to have its minimum diameter at which the components inside the flexible tube will not crush each other.

Conventionally, the minimum diameter is determined such that the following condition is satisfied.

$\Sigma s/S$ falls within a range of 0.7–0.8, wherein $\Sigma s$ is the sum of cross-sectional areas of the components inside the flexible tube, while S represents the inner cross-sectional area of the flexible tube.

In the conventional insertion unit configured as above, when the flexible tube is repeatedly bent, the bundles of optical fibers may meander inside the flexible tube and/or may be stretched. In particular, when the optical fibers are stretched, they may be gradually broken and the amount of light for illuminating an object to be observed is lowered. It is generally said that if a rate of damaged optical fibers reaches 10%, the reduction of illumination light affects the observation performance, and that if the rate of damaged optical fibers exceeds 20%, the observation performance will be significantly damaged.

SUMMARY OF THE INVENTION

In view of the above, the present invention provides an insertion unit for an endoscope, with which the components inside the flexible tube of the insertion unit will be less damaged, and thus a good observation performance can be maintained over an extended period of time.

According to the invention, there is provided an insertion unit for an endoscope, which includes a flexible tube having an inner diameter $D_1$ and an inner cross-sectional area S, and a plurality of components inserted and arranged in said flexible tube. The plurality of components include at least one optical fiber bundle. The insertion unit is configured such that the inner diameter $D_1$ is not less than 6.5 mm and the inner cross-sectional area S satisfies the condition of $0.5 \leq \Sigma s/s \leq 0.6$, where $\Sigma s$ represents a sum of cross-sectional areas of the components arranged in the flexible tube. Alternatively, the insertion unit is configured such that the inner diameter $D_1$ is less than 6.5 mm and the inner cross-sectional area S satisfies the condition of $0.5 \leq \Sigma s/s \leq 0.65$.

The inner diameter $D_1$ of the flexible tube may be the inner diameter at the narrowest portion thereof.

The insertion unit according to the invention may also include a bendable member that is connected to a distal end of the flexible tube and remotely controlled to be bent by an operation unit connected to a proximal end of the flexible tube. In this case, the inner diameter $D_1$ may be the inner diameter in the vicinity of a position where the bendable member is connected to the flexible tube.

BRIEF DESCRIPTION OF THE ACCOMPANYING DRAWINGS

DETAILED DESCRIPTION OF THE EMBODIMENTS

Hereinafter, embodiments according to the present invention will be described with reference to the accompanying drawings.

Figure 1:
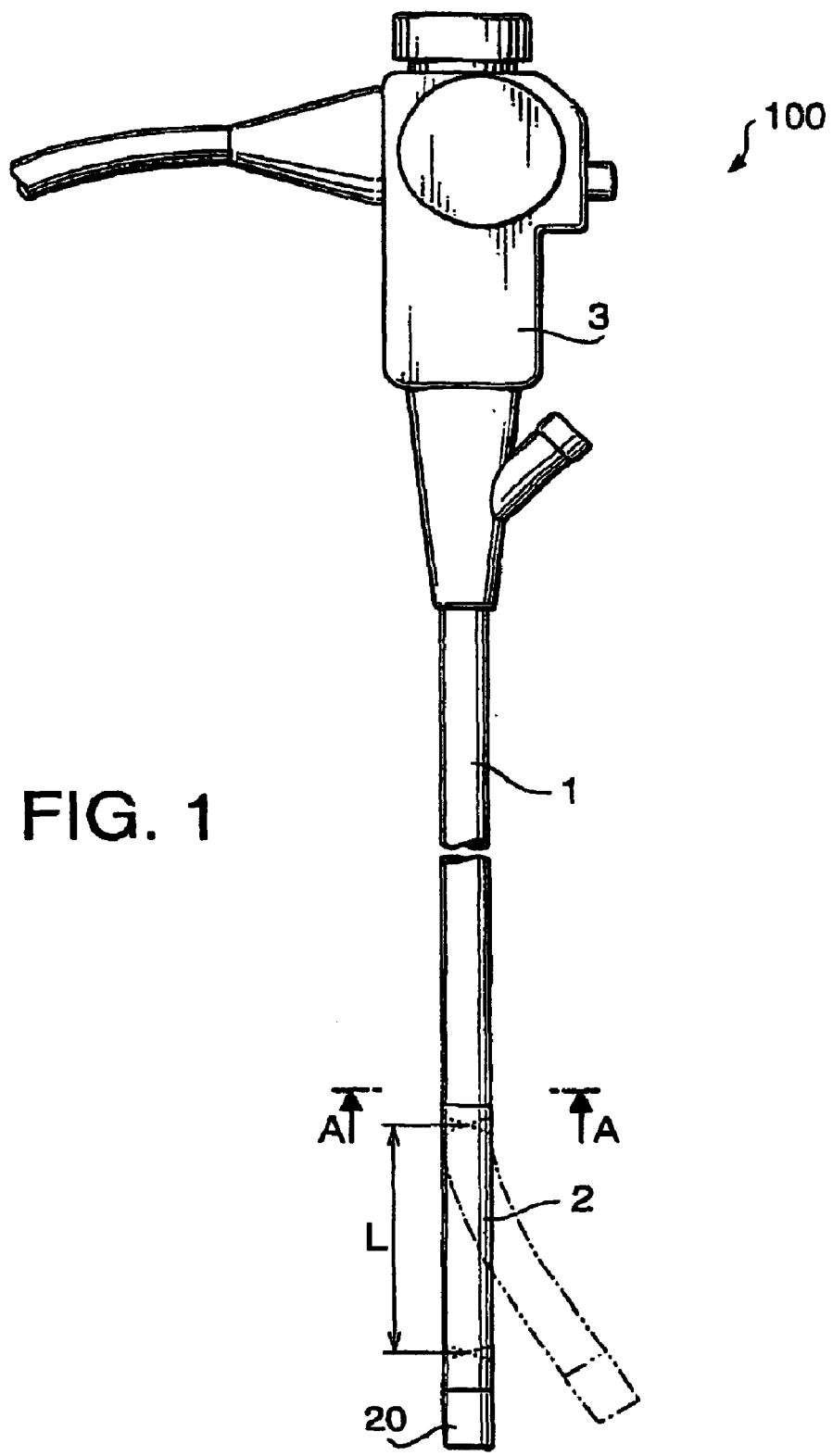
FIG. 1 shows an endoscope to which the embodiments of the invention is applicable.

FIG. 1 shows an endoscope 100 to which insertion unit according to each of embodiments of the present invention is applicable.

The endoscope 100 includes an insertion unit, which includes a flexible tube 1, a bendable member 2, an operation unit 3 and an optical unit 20.

The flexible tube 1 to be inserted into a human cavity. A proximal end of the flexible tube 1 is connected with a bottom of the operation unit 3, and a distal end of the flexible tube 1 is connected with a bendable member 2. The bendable member 2 is remotely controlled, at the operation unit 3, to bend using wires which will be described later. A reference "L" in FIG. 1 indicates a practical length of the bendable member 2, that is, the length of an actually bendable portion of the bendable member 2. The optical unit 20, which accommodates an objective optical system, is mounted at the distal end of the bendable member 2.

Figure 2:
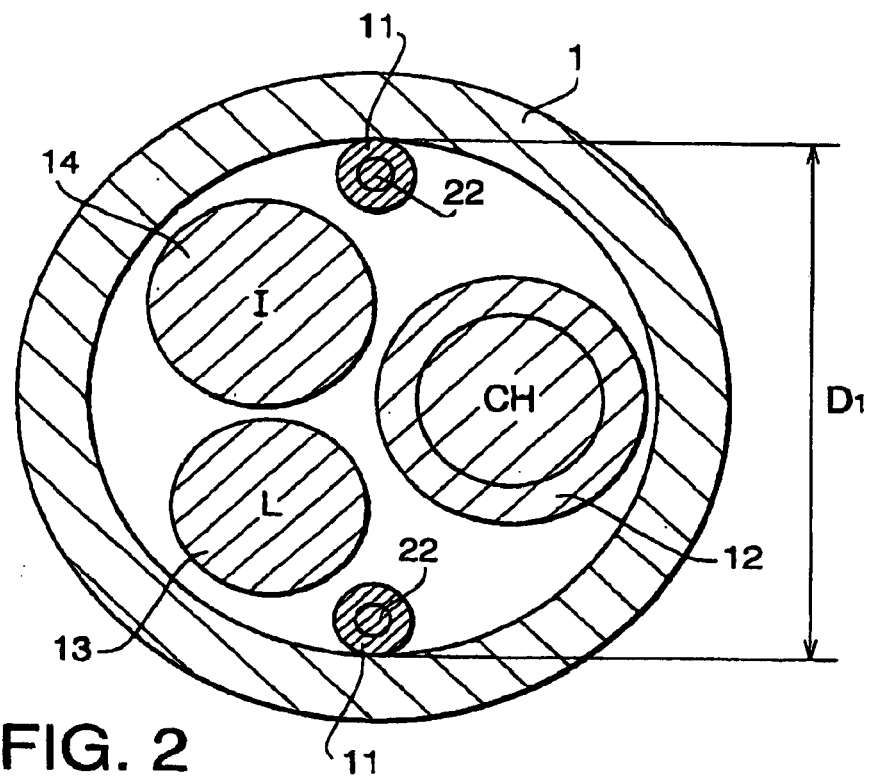
FIGS. 2 through 9 show cross-sections of a flexible tube according to first through eighth embodiments, respectively.

FIG. 2 is a cross-sectional view of the flexible tube 1 according to a first embodiment of the invention. The cross-sectional view of FIG. 2 is taken along a plane A—A which is perpendicular to a longitudinal axis of the flexible tube 1, in the vicinity of a position where the flexible tube 1 is connected with the bendable member 2. It should be noted that the flexible tube 1 is at its narrowest on the plane A—A.

The flexible tube 1 has an inner diameter $D_1$, of 2.2 mm in a plane shown in FIG. 2. A plurality of components are arranged in an inner space of the flexible tube 1. In this example shown in FIG. 2, the flexible tube 1 is configured such that two guide coils 11, a treatment accessory insertion channel 12, an illuminating optical fiber bundle 13, and an image transmitting optical fiber bundle 14 are inserted therein.

The treatment accessory insertion channel 12 is a tube made from tetrafluoroethylene resin, for example. The illuminating optical fiber bundle 13 is a bundle of optical fibers whose diameters is 30 $\mu$m, and the image transmitting optical fiber bundle 14 is a bundle of optical fibers whose diameters is 10 $\mu$m.

The two guide coils 11 are inserted through the flexible tube 1 and arranged on an inner circumferential surface of the flexible tube 1 at an interval of 180° so that the guide coils 11 are arranged symmetrically with respect to the longitudinal axis of the flexible tube 1. Wires 22 for bending the bendable member 2 are slidably inserted through each of the guide coils 11. The bendable member 2 can be bent in opposite directions (e.g., up and down in FIG. 2) by operating the operation unit 3 so that one of the wire 22 is extended while the other is retracted.

In the first embodiment, the length L of the bendable member 2 is 11 mm and the maximum bending angle of the bendable member 2 is 90° in each of the opposite directions (e.g., up and down directions in FIG. 2).

Further, an inner diameter of the bendable member 2 is substantially the same as the inner diameter $D_1$ of the flexible tube 1.

An experiment is carried out to bend the insertion unit of the flexible tube 1 shown in FIG. 2 for examining durability of the illuminating optical fiber bundle 13. In this experiment, the flexible tube 1 is kept straight, and only the bendable member 2 is bent, in opposite directions, to its maximum bending angle by 6000 times in each direction.

Generally, the bendable member 2 is bent by 10–12 times in each direction during one endoscopic inspection. Thus, bending the bendable member 2 for 6000 times in each direction may corresponds to 500–600 times of endoscopic inspection.

The bending test is carried out by varying a ratio $\Sigma s/S$, where $\Sigma s$ is the sum of cross-sectional areas of the components arranged in the inner space of the flexible tube 1, and S is the cross-sectional area of the inner space of the flexible tube 1 at the plane shown in FIG. 2. The ratio $\Sigma s/S$ is changed by varying the outer diameter of the components arranged in the flexible tube 1, i.e., the guide coils 11, the treatment accessory insertion channel 12, the illuminating optical fiber bundle 13 and/or the image transmitting optical fiber bundle 14, while keeping the inner diameter $D_1$ of the flexible tube 1 maintained constant. The combination of the diameters of the above mentioned components, the ratio $\Sigma s/S$ and the results of the experiments are shown in Table 1.

TABLE 1

|  | test No. | | | |
| --- | --- | --- | --- | --- |
|  | 1 | 2 | 3 | 4 |
| $D_{11}$ [mm] | 0.4 | 0.4 | 0.4 | 0.4 |
| $D_{12}$ [mm] | 1.05 | 1.05 | 1.1 | 1.2 |
| $D_{13}$ [mm] | 0.7 | 0.9 | 0.9 | 0.9 |
| $D_{14}$ [mm] | 0.8 | 0.9 | 0.9 | 0.9 |
| $\Sigma s/S$ [%] | 53 | 63 | 65 | 70 |
| results | A | A | B | D |

In table 1, $D_{11}$, $D_{12}$, $D_{13}$ and $D_{14}$ represent the outer diameters of the guide coil 11, the treatment accessory insertion channel 12, the illuminating optical fiber bundle 13 and the image transmitting optical fiber bundle 14, respectively. The results show ratios of broken fibers in the illuminating optical fiber bundle 13 after the bending test is carried out.

The result is indicated in four levels (A)–(D) which are defined as:
(A) the rate of broken fibers is less than 5%;
(B) the rate is more than 5% but less than 10%;
(C) the rate is more than 10% but less than 20%; and
(D) the rate is more than 20%.

It should be noted that the above definition of the levels also apply to the other tables.

Generally, the observing performance of the endoscope 100 is not seriously affected if the ratio of the broken fibers in the Illuminating optical fiber bundle 13 is less than 10%, but is affected if the ratio is over 10%, and seriously affected if the ratio is over 20%. Thus, it is preferable to keep the ratio of the broken fibers less than 10%.

As can be seen in Table 1, if the flexible tube 1 has an inner diameter $D_1$ of 2.2 mm, the ratio of the broken fibers in the illuminating optical fiber bundle 13 becomes less than 10% if $\Sigma s/S \leq 0.65$ is satisfied.

Figure 3:
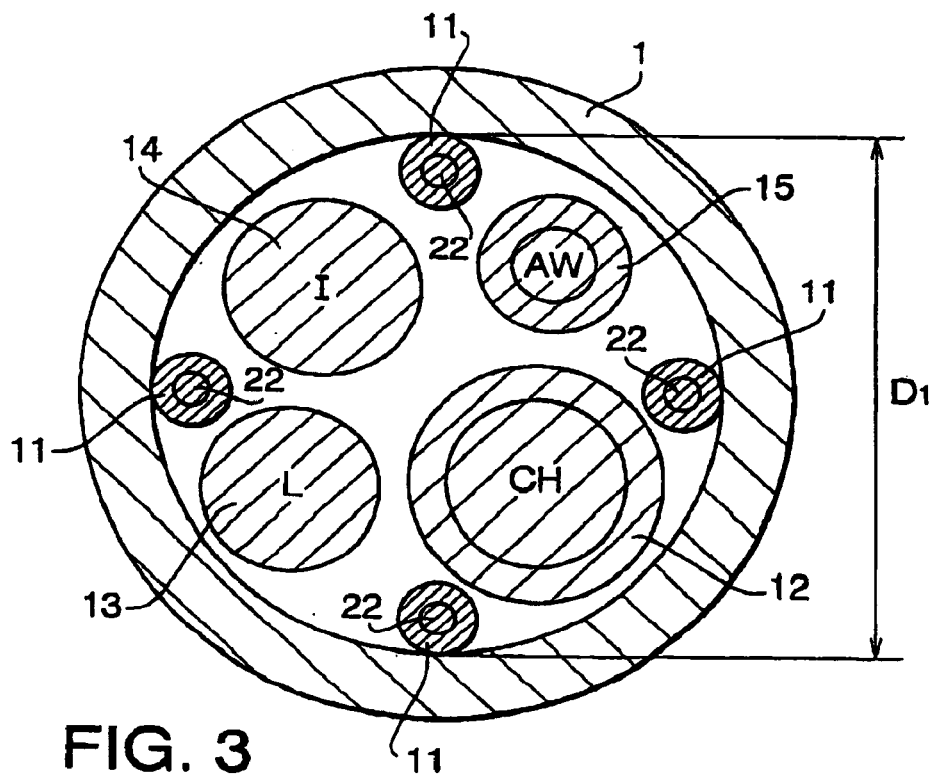

FIG. 3 is a cross sectional view of the flexible tube 1 according to a second embodiment of the invention, taken along a plane A—A perpendicular to the axis of the flexible tube 1 at a position in the vicinity of the distal end thereof. In this embodiment, four guide coils 11 are inserted through the flexible tube 1 and arranged on the inner circumferential surface of the flexible tube 1 at an interval of 90°0. Further, the treatment accessory insertion channel 12, the illuminating optical fiber bundle 13, the image transmitting optical fiber channel 14 and an air/water feeding tube 15, made from tetrafluoroethylene resin or polyurethane resin, are inserted and arranged in the inner space of the flexible tube 1.

The diameter $D_1$ of the flexible tube 1 on the plane shown in FIG. 3 is 4.45 mm, and the practical length L of the bendable member 2 is 39 mm. The maximum bending angle of the bendable member 2 is 180° in up and down directions in FIG. 3, and 160° in right and left directions (in FIG. 3).

The bending experiment is carried out in the same manner as in the first embodiment, except that the flexible tube of FIG. 3 is used. That is, the bendable member 2 is bent in up and down directions of FIG. 3 to the maximum bending angle by 6000 times in each direction. Results of the experiment are shown in table 2.

TABLE 2

|  | test No. | | | |
| --- | --- | --- | --- | --- |
|  | 1 | 2 | 3 | 4 |
| $D_{11}$ [mm] | 0.6 | 0.6 | 0.6 | 0.6 |
| $D_{12}$ [mm] | 2.3 | 2.4 | 2.5 | 2.5 |
| $D_{13}$ [mm] | 1.5 | 1.5 | 1.5 | 1.5 |
| $D_{14}$ [mm] | 1.5 | 1.5 | 1.5 | 1.6 |
| $D_{15}$ [mm] | 1.2 | 1.2 | 1.2 | 1.3 |
| $\Sigma s/S$ [%] | 64 | 66 | 69 | 72 |
| results | A | A | C | D |

In table 2, $D_{15}$ represents the outer diameter of the air/water feeding tube 15. Note that $\Sigma s$ in table 2 also includes a cross-sectional area of the air/water feeding tube 15.

As can be seen in table 2, if the flexible tube has an inner diameter $D_1$ of 4.45 mm, the ratio of broken fibers in the illuminating optical fiber bundle 13 becomes less than 10%, and therefore the observation performance of the endoscope 100 will not be seriously affected, if $\Sigma s/S \leq 0.66$ is satisfied.

Figure 4:
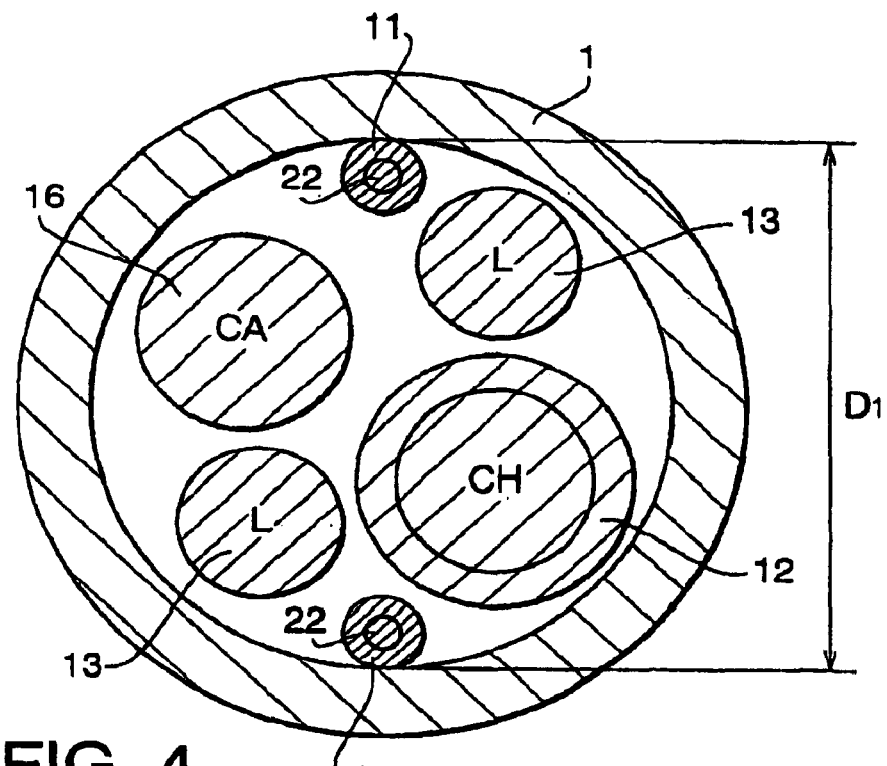

FIG. 4 is a cross sectional view of the flexible tube 1 according to a third embodiment of the invention, taken along a plane A—A which is perpendicular to the axis of the flexible tube 1, at a position in the vicinity of the distal end thereof. In this embodiment, two guide coils 11 are inserted through the flexible tube 1 and arranged on the inner circumferential surface at an interval of 180°. Further, the treatment accessory insertion channel 12, two illuminating optical fiber bundles 13 and an image signal transmitting cable 16 are inserted and arranged in the inner space of the flexible tube 1.

The diameter $D_1$ of the flexible tube 1 on the plane shown in FIG. 4 is 4.4 mm, and the practical length L of the bendable member 2 is 32 mm. The maximum bending angle of the bendable member 2 is 180° in an upward direction and 130° in a downward direction.

The bending experiment is carried out in the same manner as in the first embodiment, except that the flexible tube 1 of FIG. 4 is used. Results of the experiment are shown in table 3.

TABLE 3

|  | test No. | | |
| --- | --- | --- | --- |
|  | 1 | 2 | 3 |
| $D_{11}$ [mm] | 0.63 | 0.63 | 0.63 |
| $D_{12}$ [mm] | 2.3 | 2.5 | 2.5 |
| $D_{13}$ [mm] | 1.3 | 1.3 | 1.5 |
| $D_{16}$ [mm] | 1.6 | 1.6 | 1.6 |
| Σs/S [%] | 62 | 67 | 73 |
| results | A | B | D |

In table 3, $D_{16}$ represents the outer diameter of the image signal transmitting cable 16. Note that Σs in table 3 is the sum of the cross-sectional areas of the guide coils 11, the treatment accessory insertion channel 12, the illuminating optical fiber bundles 14 and the image signal transmitting cable 16.

As can be seen in table 3, in the case the flexible tube has an inner diameter $D_1$ of 4.4 mm, the rate of broken fibers in the illuminating optical fiber bundle 13 becomes less than 10% if Σs/S≦0.67 is satisfied.

Figure 5:
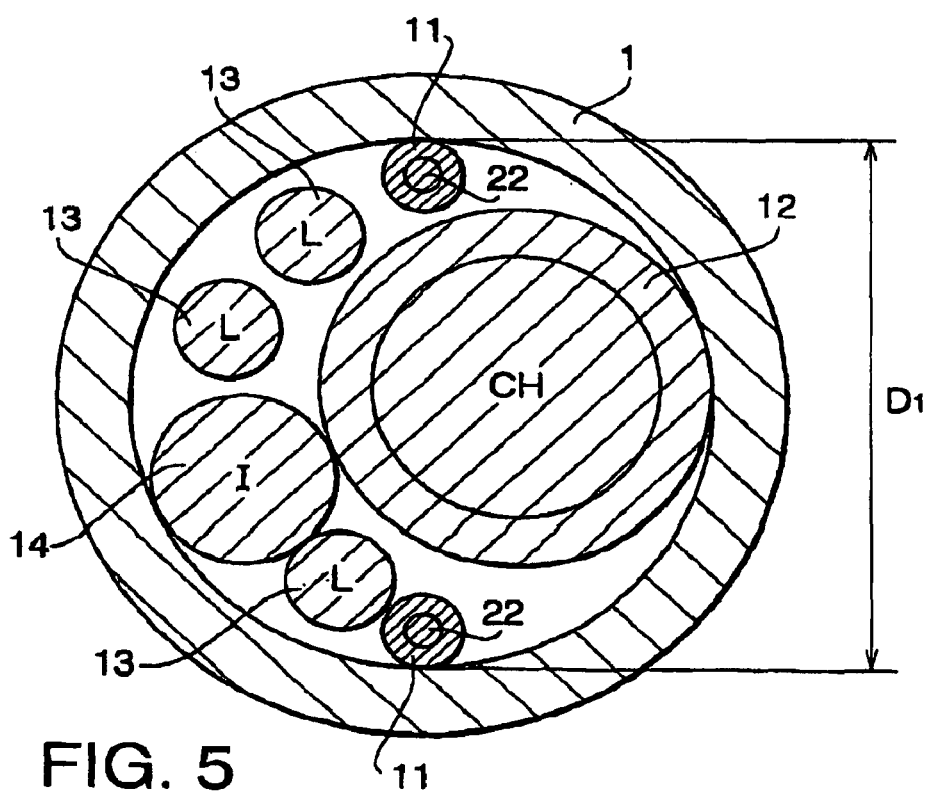

FIG. 5 is a cross sectional view of the flexible tube 1 according to a fourth embodiment of the invention, taken along a plane A—A which is perpendicular to the axis of the flexible tube 1, at a position in the vicinity of the distal end thereof. In this embodiment, two guide coils 11 are inserted through the flexible tube 1 and arranged on the inner circumferential surface at an interval of 180°. Further, the treatment accessory insertion channel 12, three illuminating optical fiber bundles 13 and the image transmitting optical fiber bundle 14 are inserted and arranged in the rest of the inner space of the flexible tube 1. Note that Σs in the present embodiment represents the sum of the cross-sectional areas of the above mentioned components (11, 12, 13, 14) that are arranged in the flexible tube 1.

The diameter $D_1$ of the flexible tube 1 at the plane shown in FIG. 5 is 5.35 mm, and the practical length L of the bendable member 2 is 33 mm. The maximum bending angle of the bendable member 2 is 180° in both the up and down directions of FIG. 5.

The bending experiment is carried out in the same manner as in the first embodiment, except that the flexible tube 1 of FIG. 5 is used. Results of the experiment are shown in table 4.

TABLE 4

|  | test No. | | |
| --- | --- | --- | --- |
|  | 1 | 2 | 3 |
| $D_{11}$ [mm] | 0.8 | 0.8 | 0.8 |
| $D_{12}$ [mm] | 3.6 | 3.8 | 3.9 |
| $D_{13}$ [mm] | 0.9 | 0.9 | 0.95 |
| $D_{14}$ [mm] | 1.4 | 1.4 | 1.4 |
| Σs/S [%] | 65 | 70 | 74 |
| results | A | C | D |

As can be seen in table 4, if the flexible tube has an inner diameter $D_1$ of 5.35 mm, the ratio of broken fibers in the illuminating optical fiber bundle 13 becomes less than 10% if Σs/S≦0.65 is satisfied.

Figure 6:
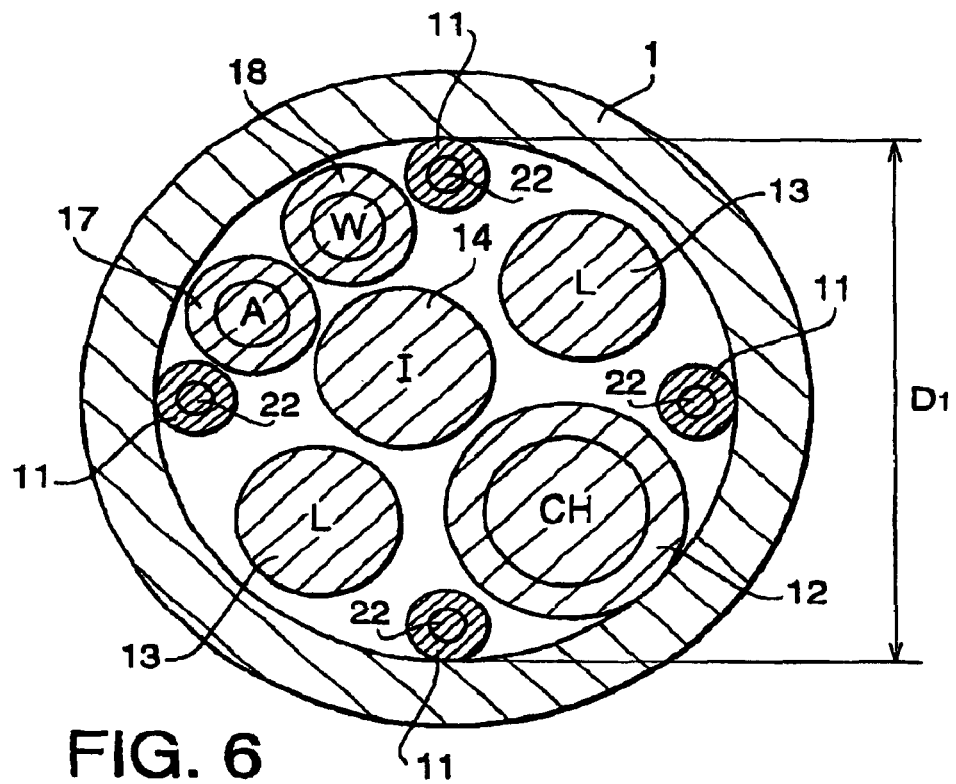

FIG. 6 is a cross sectional view of the flexible tube 1 according to a fifth embodiment taken along a plane A—A which is perpendicular to the axis of the flexible tube 1 in the vicinity of the distal end thereof. In this embodiment, four guide coils 11 are inserted through the flexible tube 1 and arranged on the inner circumferential surface at an interval of 90°. Further, the treatment accessory insertion channel 12, two illuminating optical fiber bundles 13, the image transmitting optical fiber bundle 14, an air feeding tube 17 and a water feeding tube 18 are inserted and arranged in the inner space of the flexible tube 1. Note that Σs in the present embodiment represents the sum of the cross-sectional areas of the above-mentioned components (11, 12, 13, 14, 17, 18) that are arranged in the flexible tube 1.

The diameter $D_1$ of the flexible tube 1 on the plane shown in FIG. 6 is 6.4 mm, and the practical length L of the bendable member 2 is 40 mm. The maximum bending angle of the bendable member 2 is 180° in the up and down directions, and 100° in the right and left directions in FIG. 6.

The bending experiment is carried out in the same manner as in the first embodiment except that the flexible tube 1 of FIG. 6 is used. Results of the experiment are indicated in table 5.

TABLE 5

|  | test No. | | |
| --- | --- | --- | --- |
|  | 1 | 2 | 3 |
| $D_{11}$ [mm] | 1.1 | 1.1 | 1.1 |
| $D_{12}$ [mm] | 2.6 | 2.6 | 2.6 |
| $D_{13}$ [mm] | 1.8 | 2 | 2 |
| $D_{14}$ [mm] | 1.8 | 1.8 | 2 |
| $D_{17}$ [mm] | 1.5 | 1.5 | 1.5 |
| $D_{18}$ [mm] | 1.4 | 1.4 | 1.4 |
| Σs/S [%] | 62 | 66 | 68 |
| results | A | B | D |

As can be seen in table 5, when the flexible tube has an inner diameter $D_1$ of 6.4 mm, the rate of broken fibers in the illuminating optical fiber bundle 13 becomes less than 10% if Σs/S≦0.66 is satisfied.

Figure 7:
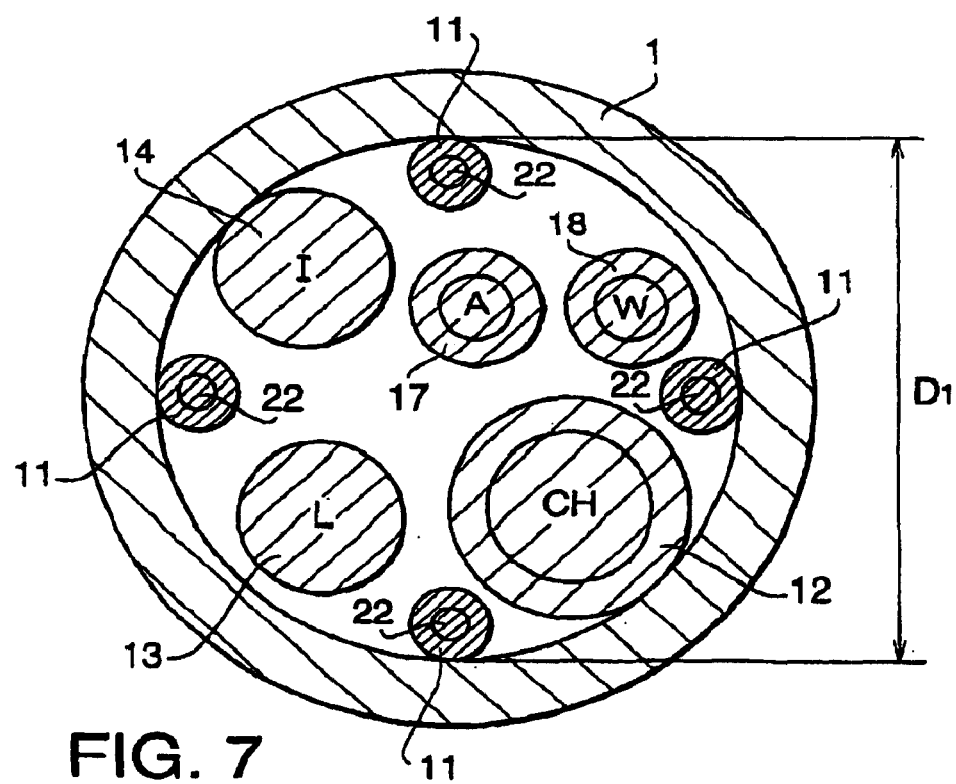

FIG. 7 is a cross sectional view of the flexible tube 1 according to a sixth embodiment of the invention, taken along a plane A—A in the vicinity of the distal end and perpendicular to the axis of the flexible tube 1. In this embodiment, four guide coils 11 are inserted through the flexible tube 1 and arranged on the inner circumferential surface at an interval of 90°. Further, the treatment accessory insertion channel 12, the illuminating optical fiber bundle 13, the image transmitting optical fiber bundle 14, the air feeding tube 17 and the water feeding tube 18 are inserted and arranged in the inner space of the flexible tube 1. Note that Σs in the present embodiment represents the sum of the cross-sectional areas of the above-mentioned components (11, 12, 13, 14, 17, 18) arranged in the flexible tube 1.

The diameter $D_1$ of the flexible tube 1 on the plane shown in FIG. 7 is 6.7 mm, and the practical length L of the bendable member 2 is 42 mm. The maximum bending angle of the bendable member 2 is 180° in the up and down directions, and 100° in the right and left directions in FIG. 7.

The experiment is carried out in the same manner as in the first embodiment except that the flexible tube of FIG. 7 is used. Results of the experiment are shown in table 6.

TABLE 6

| | test No. | | | | |
|---|---|---|---|---|---|
| | 1 | 2 | 3 | 4 | 5 |
| $D_{11}$ [mm] | 1.1 | 1.1 | 1.1 | 1.1 | 1.1 |
| $D_{12}$ [mm] | 2.7 | 2.7 | 3 | 2.7 | 3 |
| $D_{13}$ [mm] | 2.1 | 2.4 | 2.1 | 2.5 | 2.5 |
| $D_{14}$ [mm] | 2.1 | 2.1 | 2.1 | 2.5 | 2.5 |
| $D_{17}$ [mm] | 1.6 | 1.6 | 1.6 | 1.6 | 1.6 |
| $D_{18}$ [mm] | 1.3 | 1.3 | 1.3 | 1.3 | 1.3 |
| $\Sigma s/S$ [%] | 56 | 59 | 60 | 64 | 68 |
| results | A | B | B | C | D |

As can be seen in table 6, when the flexible tube has an inner diameter $D_1$ of 6.7 mm, the ratio of broken fibers in the illuminating optical fiber bundle 13 becomes less than 10% if $\Sigma s/S \leq 0.6$ is satisfied.

Figure 8:
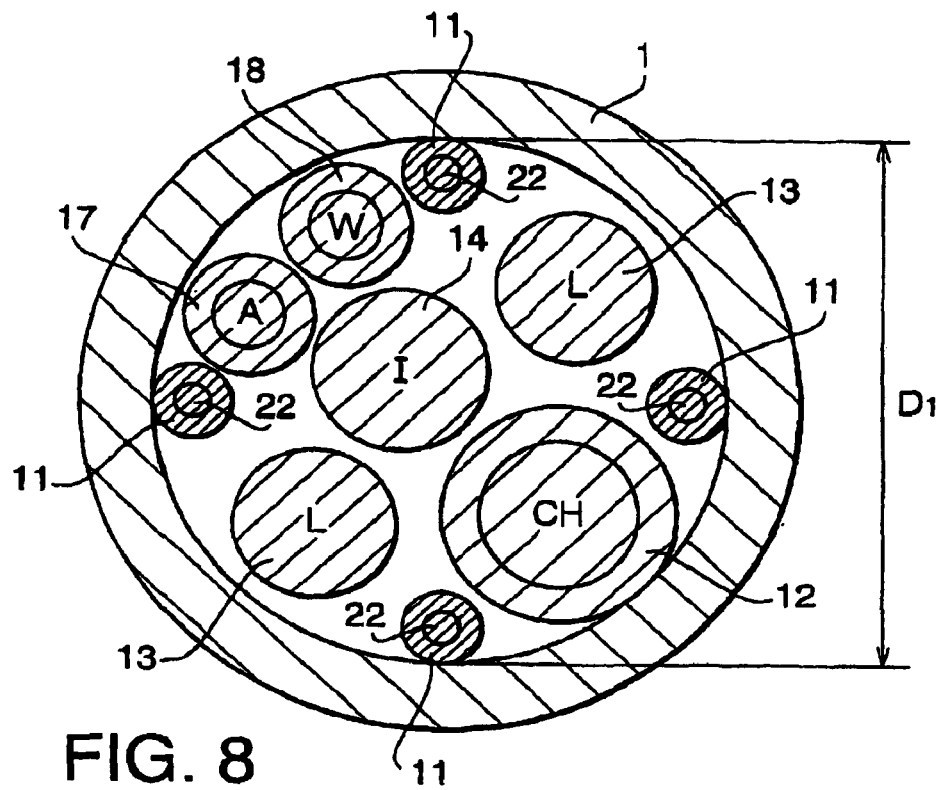

FIG. 8 is a cross sectional view of the flexible tube 1 according to a seventh embodiment, taken along a plane A—A perpendicular to the axis of the flexible tube 1 in the vicinity of the distal end thereof. In this embodiment, four guide coils 11 are inserted through the flexible tube 1 and arranged on the inner circumferential surface at an interval of 90°. Further, the treatment accessory insertion channel 12, two illuminating optical fiber bundle 13, the image transmitting optical fiber bundle 14, the air feeding tube 17 and the water feeding tube 18 are inserted and arranged in the rest of the inner space of the flexible tube 1. Note that $\Sigma s$ in the present embodiment represents the sum of the cross-sectional areas of the above-mentioned components (11, 12, 13, 14, 17, 18) arranged in the flexible tube 1.

The diameter $D_1$ of the flexible tube 1 on the plane shown in FIG. 8 is 7.8 mm, and the practical length L of the bendable member 2 is 48 mm. The maximum bending angle of the bendable member 2 is 210° for bending upwards, 120° for bending downwards, and 120° for bending right and left.

The experiment is carried out in the same manner as in the first embodiment except that the flexible tube 1 of FIG. 8 is used. Results of the experiment are shown in table 7.

TABLE 7

| | test No. | | | |
|---|---|---|---|---|
| | 1 | 2 | 3 | 4 |
| $D_{11}$ [mm] | 1.2 | 1.2 | 1.2 | 1.2 |
| $D_{12}$ [mm] | 3 | 3 | 3.5 | 3.5 |
| $D_{13}$ [mm] | 2.2 | 2.5 | 2.2 | 2.5 |
| $D_{14}$ [mm] | 2.4 | 2.4 | 2.4 | 2.4 |
| $D_{17}$ [mm] | 1.6 | 1.6 | 1.6 | 1.6 |
| $D_{18}$ [mm] | 1.6 | 1.6 | 1.6 | 1.6 |
| $\Sigma s/S$ [%] | 58 | 62 | 63 | 68 |
| results | A | B | C | D |

As can be seen in table 7, when the flexible tube has an inner diameter $D_1$ of 7.8 mm, the ratio of broken fibers in the illuminating optical fiber bundle 13 becomes less than 10% and therefore the observation performance of the endoscope 100 will be not seriously affected, if $\Sigma s/S \leq 0.62$ is satisfied.

Figure 9:
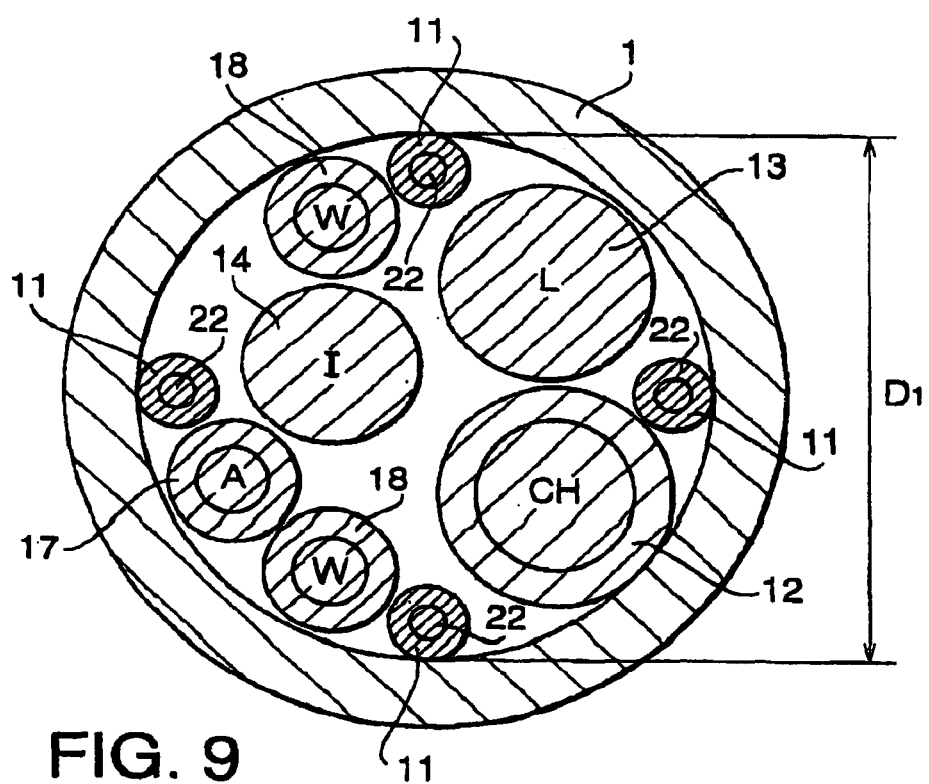

FIG. 9 is a cross sectional view of the flexible tube 1 according to a eighth embodiment of the invention, taken along a plane perpendicular to the axis of the flexible tube 1, at a position in the vicinity of the distal end thereof. In this embodiment, four guide coils 11 are inserted through the flexible tube 1 and arranged on the inner circumferential surface at an interval of 90°. Further, the treatment accessory insertion channel 12, the illuminating optical fiber bundle 13, the image transmitting optical fiber bundle 14, the air feeding tube 17 and two water feeding tube 18 are inserted and arranged in the rest of the inner space of the flexible tube 1. Note that $\Sigma s$ in the present embodiment represents the sum of the cross-sectional areas of the above-mentioned components (11, 12, 13, 14, 17, 18) that are arranged in the flexible tube 1.

The diameter $D_1$ of the flexible tube 1 on the plane shown in FIG. 9 is 9.3 mm, and the practical length L of the bendable member 2 is 75 mm. The maximum bending angle of the bendable member 2 is 180° in the up and down directions, and in the right and left directions.

The bending test is carried out in the same manner as in the first embodiment except that the flexible tube 1 of FIG. 9 is used. Results of the tests are shown in table 8.

TABLE 8

| | test No. | | | | |
|---|---|---|---|---|---|
| | 1 | 2 | 3 | 4 | 5 |
| $D_{11}$ [mm] | 1.4 | 1.4 | 1.4 | 1.4 | 1.4 |
| $D_{12}$ [mm] | 3.2 | 3.8 | 4.2 | 4.2 | 4.5 |
| $D_{13}$ [mm] | 3 | 3.5 | 3.7 | 4 | 4 |
| $D_{14}$ [mm] | 2.8 | 3 | 3.1 | 3.5 | 3.5 |
| $D_{17}$ [mm] | 1.7 | 1.7 | 1.7 | 1.7 | 1.7 |
| $D_{18}$ [mm] | 1.7 | 1.7 | 1.7 | 1.7 | 1.7 |
| $\Sigma s/S$ [%] | 50 | 60 | 66 | 72 | 75 |
| results | A | A | C | D | D |

As can be seen in table 6, in the case the flexible tube has an inner diameter $D_1$ of 9.3 mm, the rate of broken fibers in the illuminating optical fiber bundle 13 becomes less than 10% if $\Sigma s/S \leq 0.6$ is satisfied.

Figure 10:
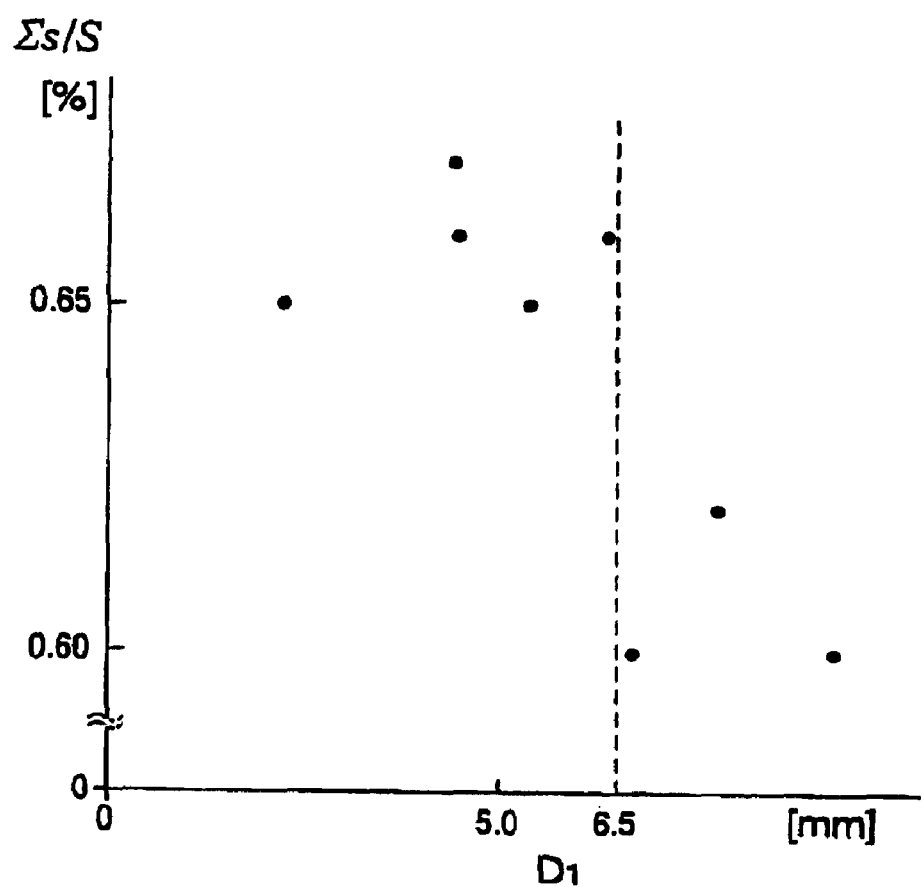
FIG. 10 is a graph showing the relation between a diameter of the flexible tube, $D_1$, and a maximum value of $\Sigma s/S$ by which a rate of damaged fibers in an illuminating optical fiber bundle is less than 10%.

FIG. 10 is a graph showing the relation between the diameter of the flexible tube, $D_1$, and the maximum value of $\Sigma s/S$ by which the rate of broken fibers in the illuminating optical fiber bundle 13 is less than 10% after the bending test is carried out. It can be seen from FIG. 10 that $\Sigma s/S \leq 0.65$ is sufficient for keeping the rate of broken fibers less than 10% if the diameter of the flexible tube 1, $D_1$, is less than 6.5 mm. However, $\Sigma s/S \leq 0.6$ is required if the diameter $D_1$ is not less than 6.5 mm.

Though the minimum value of the ratio $\Sigma s/S$ is not limited from the point of view of preventing the optical fibers from being broken by bending the bendable member 2, the ratio $\Sigma s/S$ should not be too small, preferably not less than 0.5, since the outer diameter of the flexible tube is required to be as small as possible to decrease pain inflicted on a patient during an endoscope inspection. Thus, a proper range of $\Sigma s/S$ may be $0.5 \leq \Sigma s/S \leq 0.65$ for a flexible tube having an inner diameter $D_1$ less than 6.5 mm, and $0.5 5 \leq \Sigma s/S \leq 0.60$ for a flexible tube having an inner diameter $D_1$ not less than 6.5 mm.

As above, according to the embodiments, an insertion unit for an endoscope is configured such that the following condition is satisfied.

$$0.5 \leq \Sigma s/S \leq 0.6$$

where, S represents an area of an inner cross-section of a hollow flexible tube for an endoscope, in which a plurality of components are inserted, and $\Sigma s$ represents a sum of cross-sectional areas of the components arranged in the flexible tube, whose inner diameter is equal to or greater than 6.5 mm. An example of an insertion unit having a flexible tube whose inner diameter is equal to or greater than 6.5 mm is one for digestive tubes.

An insertion unit for an endoscope is configured such that the following condition:

$$0.5 \leq \Sigma s/S \leq 0.65$$

may be satisfied when the inner diameter of the flexible tube is less than 6.5 mm. An example of an insertion unit having a flexible tube whose inner diameter is less than 6.5 mm is one for bronchial tubes.

The present disclosure relates to the subject matter contained in Japanese Patent Application No. P2001-007177, filed on Jan. 16, 2001, which is expressly incorporated herein by reference in its entirety.

What is claimed is:

1. An insertion unit for an endoscope, comprising:
   a flexible tube having an inner diameter $D_1$ and an inner cross-sectional area S; and
   a plurality of components inserted and arranged inside said flexible tube inner diameter, said components including an optical fiber bundle,
   wherein, said inner diameter $D_1$ is not less than 6.5 mm and said inner cross-sectional area S satisfies a condition:

$$0.5 \leq \Sigma s/S \leq 0.6$$

where $\Sigma s$ represents a sum of cross-sectional areas of said components arranged inside said flexible tube inner diameter.

2. The insertion unit according to claim 1, wherein said inner diameter $D_1$ is the inner diameter at the narrowest portion of said flexible tube.

3. The insertion unit according to claim 1, comprising a bendable member connected to said flexible tube, said bendable member being bent with said plurality of components inserted therein, said inner diameter $D_1$ being the inner diameter in the vicinity of where said bendable member is connected to said flexible tube.

4. An insertion unit of an endoscope, comprising:
   a flexible tube having an inner diameter $D_1$ and an inner cross-sectional area S; and
   a plurality of components inserted and arranged inside said flexible tube inner diameter, said components including an optical fiber bundle,
   wherein, said inner diameter $D_1$ is less than 6.5 mm and said inner cross-sectional area S satisfies a following condition:

$$0.5 \leq \Sigma s/S \leq 0.65,$$

where $\Sigma s$ represents a sum of cross-sectional areas of said components arranged inside said flexible tube inner diameter.

5. The insertion unit according to claim 4, wherein said inner diameter $D_1$ is the inner diameter at the narrowest portion of said flexible tube.

6. The insertion unit according to claim 5, comprising a bendable member connected to a distal end of said flexible tube, said bendable member being bent with said plurality of components inserted therein, said inner diameter $D_1$ being the inner diameter in the vicinity of a position where said bendable member is connected to said flexible tube.

* * * * *